| United States Patent [19] | [11] Patent Number: 4,795,594 |
|---|---|
| Dankowski | [45] Date of Patent: Jan. 3, 1989 |

[54] PROCESS FOR THE PRODUCTION OF WATER INSOLUBLE PEROXYCARBOXYLIC ACIDS

[75] Inventor: Manfred Dankowski, Karlstein, Fed. Rep. of Germany

[73] Assignee: Degussa Aktiengesellschaft, Frankfurt am Main, Fed. Rep. of Germany

[21] Appl. No.: 615,303

[22] Filed: May 30, 1984

[30] Foreign Application Priority Data

Jun. 7, 1983 [DE] Fed. Rep. of Germany ....... 3320497

[51] Int. Cl.$^4$ ............................................ C07C 179/10
[52] U.S. Cl. ................................................ 260/502 R
[58] Field of Search ..................................... 260/502 R

[56] References Cited

U.S. PATENT DOCUMENTS

| 3,845,112 | 10/1974 | Waldmann et al. | 260/502 R |
| 4,119,660 | 10/1978 | Hutchins | 260/502 R |
| 4,172,086 | 10/1979 | Berkowitz | 260/502 R |
| 4,287,135 | 9/1981 | Stober et al. | 260/502 R |
| 4,370,251 | 1/1983 | Liao | 260/502 R |

FOREIGN PATENT DOCUMENTS

| 37146 | 10/1981 | European Pat. Off. . |
| 45290 | 2/1982 | European Pat. Off. . |

*Primary Examiner*—Bruce D. Gray
*Attorney, Agent, or Firm*—Cushman, Darby & Cushman

[57] ABSTRACT

The strong foaming which occurs during the reaction of a carboxylic acid, aqueous hydrogen peroxide and sulfuric acid as well as when a phlegmatizing additive is also employed is greatly reduced by adding a phosphane oxide. Besides a local gathering of alkali during the subsequent neutralization of the sulfuric acid is prevented and the flowability of the suspension obtained of the product is improved. Furthermore, the product obtained has remarkable storage stability.

38 Claims, No Drawings

PROCESS FOR THE PRODUCTION OF WATER INSOLUBLE PEROXYCARBOXYLIC ACIDS

BACKGROUND OF THE INVENTION

Peroxycarboxylic acids are employed not only as oxidizing agents in organic syntheses but also in the washing and/or bleaching of textiles since their activity occurs already below 80° C., see for example European published application No. 37146 and Liao U.S. Pat. No. 4,370,251.

However, since solid water insoluble peroxycarboxylic acid in the pure or highly concentrated state are thermally and mechanically sensitive they have been handled in the past with phlegmatizers or stabilizers and thereby among the foremost employed are derivatives of phosphoric acid, phosphorous acid, and phosphonic acid, see e.g. European published application No. 37146, as well as diverse salts of various mineral acids, see e.g. Belgian patent No. 560389 and European published application No. 48290.

Of course, the difficulties which occur in the reaction of a water insoluble carboxylic acid and aqueous hydrogen peroxide in the presence of an acid, thus in a suspension, have been thoroughly investigated, but the solutions proposed are very expensive industrially, see e.g. Berkowitz U.S. Pat. No. 4,172,086 and European published application No. 45290 and related Liao U.S. Pat. No. 4,370,251.

In the production of higher water insoluble peroxycarboxylic acids, from about $C_6$ it has proven to be very disturbing that the reaction mixture of hydrogen peroxide, water insoluble carboxylic acid and acid exhibits a greatly increasing foam formation with increasing molecular weight of the carboxylic acid as a result of which the handling of this reaction mixture is made most difficult.

The problem of the present invention therefore is to produce higher peroxycarboxylic acids from $C_6$ in an industrially simpler manner.

SUMMARY OF THE INVENTION

It has now been found that this problem in the production of water insoluble peroxycarboxlic acids having 6 to 16 carbon atoms can be solved by reaction of the corresponding aliphatic carboxylic acids having 6 to 16 carbon atoms or the corresponding aromatic carboxylic acids having 7 to 9 carbon atoms with hydrogen peroxide in the presence of water, sulfuric acid and optionally an additive if the reaction is carried out in the presence of a phosphane oxide of the formula

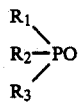

where $R_1$, $R_2$, and $R_3$ are the same or different and are alkyl, cycloalkyl, aralkyl, or aryl.

While all phosphane oxides within the above formula can be employed in the process of the invention, a substantial improvement of the process, however, is obtained by using trialkyl phosphane oxides whose individual alkyl groups contain 6 to 10 carbon atoms, as e.g.: tri-n-hexyl-; tri-n-heptyl-; tri-n-octyl-; tri-n-nonyl-; tri-n-decyl-phosphane oxide.

Especially preferred is tri-n-octyl-phosphane oxide. As cycloalkyl-phosphane oxides there can be used for example tricyclopentylphosphane oxide or tricyclohexylphosphane oxide.

Likewise there can be used triphenylphosphane oxide and tribenzylphosphane oxide.

Additional illustrative compounds include trimethylphosphane oxide, tri-n-butylphosphane oxide, di-n-hexyl n-octylphosphane oxide, tri-n-octadecylphosphane oxide triisoctylphosphane oxide, tri sec.octylphosphane oxide and tri p-tolyphosphane oxide.

The phosphane oxide is used in an amount of 0.01 to 10 wt. %, preferably 0.1 to 7 wt. % based on the active oxygen employed.

The reaction is carried out with a molar ratio of hydrogen peroxide to carboxylic acid of 1 to 10:1, preferably 1.5 to 3:1.

There can be employed both mono and dicarboxylic acids. Especially suited are aliphatic dicarboxylic acids having a total of 9–13 carbon atoms, above all azelaic acid, dodecanedioic acid and brassylic acid.

Additional suitable carboxylic acids include alkanoic acids and alkanedioic acids such as hexanoic acid, octanoic acid, decanoic acid, lauric acid, palmitic acid, adipic acid, pimelic acid, suberic acid, sebacic acid, hexadecanedioic acid, and aromatic carboxylic acids such as benzoic acid and other aromatic hydrocarbon carboxylic acids, e.g. phthalic acid, isophthalic acid, terephthalic acid, o-toluic acid, 2,4-dimethylbenzoic acid, p-ethyl-benzoic acid, hemimellitic acid, and trimesic acid or substituted aromatic carboxylic acids, e.g. p-chlorobenzoic acid.

In carrying out the process of the invention furthermore, it has proven favorable to employ sulfuric acid and carboxylic acid in the molar ratio of 1 to 10:1, preferably 2 to 4:1.

Furthermore, it has been found that the best results are obtained by adding the phosphane oxide to a mixture of hydrogen peroxide and sulfuric acid and then to introduce the carboxylic acid into this mixture.

The reaction is carried out at a temperature between 40°–70° C., preferably at 45°–60° C.

Hydrogen peroxide is used in aqueous solutions containing 30–99% wt. %, e.g. 30–90 wt. %, preferably 40–50 wt. %. Sulfuric acid is employed in concentrations of 20–98 wt. %, preferably 90–98 wt. %.

The reaction product is separated from the reaction mixture in customary manner by filtering or centrifuging and is dried. If the product is the pure peroxycarboxylic acid itself, i.e. without the additional phlegmatization with a phlegmatizing salt then the product must be washed free of mineral acid.

The industrial advance of the process of the invention is that by the use of a phosphane oxide there is unexpectedly greatly reduced the viscosity of the reaction mixture of hydrogen peroxide, sulfuric acid, water and carboxylic acid. Thus a reaction mixture without the addition of phosphane oxide exhibits a strong foam formation which has a negative influnnce on both the wetting of the carboxylic acid with the oxidation mixture and on the establishment of an equilibrium in the reaction. In contrast when there was added trioctylphosphane oxide the viscosity was so greatly reduced that for the first time it was possible to use the reaction suspension industrially.

The mixture with the phosphane oxide was better able to be stirred, was more flowable and more pumpable. Also the residual moisture content, which normally is difficult to remove from peroxycarboxylic acid, was greatly reduced.

It is known from a scientific study that the epoxidation with peroxycarboxylic acids can be inhibited by materials such as dimethylformamide, amine oxide, phosphane oxide, or arsane oxide, see Angew Chemie Volume 94 (1982), pages 750–766.

Therefore it was completely unexpected that the use of phosphane oxide according to the invention would influence in a decisive manner the consistency of the reaction mixture.

It has further been found that the peroxycarboxylic acids formed are stabilized in outstanding manner if, before during or after the reaction there is added to the mixture an additional phlegmatizing agent.

As such phlegmatizing agents there can be used alkali, magnesium, alkaline earth or earth metal salts, e.g. sodium sulfate, potassium sulfate, magnesium sulfate, calcium sulfate, or boric acid. These materials can be added either in solid form or as aqueous solutions or suspensions. It is also possible to produce them in situ before or during the reaction and/or by adding to the precipitated product before its separation from the reaction solution.

Especially suited for this is a process in which the reaction of the water insoluble carboxylic acid with the aqueous hydrogen peroxide is carried out in the presence of a phosphane oxide at 45°–60° C., thereupon the reaction mixture is cooled to a temperature of 45°–50° C., preferably 40°–32° C. and an aqueous alkali sulfate solution is added, e.g. sodium sulfate or potassium sulfate solution, the pH of the mixture adjusted to 2–6 with the help of alkali metal hydroxide or alkali metal carbonate solution, e.g. sodium hydroxide, sodium carbonate, potassium hydroxide or potassium carbonate, and then the reaction product is worked up in known manner.

As alkali hydroxide or alkali carbonate there can be employed aqueous solutions having 5–50 wt. %, preferably 30–40 wt. % of alkali hydroxide. Of the three alkali hydroxides or carbonates there especially is employed the sodium derivative.

The above-mentioned pH of 2–6 can likewise be established after the end of the reaction for the production of the peroxycarboxylic acid by addition of corresponding amounts of magnesium hydroxide or oxide or of alkaline earth hydroxides, e.g. calcium hydroxide, as well as their carbonates, e.g. calcium carbonate, or earth metal hydroxide, as well as their carbonates, and also alkali aluminates, e.g. sodium aluminate and potassium aluminate or even sodium metaborate. These materials also can be added in dissolved or suspended form, i.e. in aqueous medium.

The additional phlegmatization agent preferably should be used in an amount of 0 to 80 wt. % based on the finished product.

The storage stability surprisingly is greatly increased by the simultaneous presence of the phosphane oxide and the phlegmatization agent. Apparently a synergistic effect of the two additives is present, see Example 2.

In using sodium sulfate which is either added as a solid or in aqueous solution, or is formed in situ (all three possibilities can even be used simultaneously) the residual moisture content of the peroxycarboxylic acid is reduced to 50% after centrifuging.

This stabilizing effect occurs especially strongly if the formation in situ of sodium sulfate from the sulfuric acid present in the reaction mixture and added soda lye is carried out at a temperature above the transforation point of sodium sulfate decahydrate to water free sodium sulfate, i.e. at a temperature beginning at 32.2°–32.4° C.

The invention is explained in connection with the following examples. Example 1 is carried out without additional stabilizer, in the presence of tricotylphosphane oxide alone. Examples 2 to 5 are carried out in the presence of additional stabilizer.

Unless otherwise indicated all parts and percentages are by weight.

The process can comprise, consist essentially of, or consist of the stated steps with the recited material.

In the Examples:
DPDA = diperoxydodecanedioic acid
AO = active oxygen content
% = weight percent.

In experiments, dodecanedioic acid was reacted with 70 wt. % hydrogen peroxide and 96 wt. % sulfuric acid in a (for example) molar ratio of 1:3:4 and there occurred a strong, stable foam, apparently through partial decomposition of hydrogen peroxide. This foam could not be broken even by stirring so that it was not possible to carry out the desired reaction in a trouble free manner, above all, this was true in a large scale experiment.

In contrast in the procedure according to the following Examples 1–9 not only was such an insignificant foam formed that it was possible to operate on a large scale without problem but also after the reaction itself in the subsequent neutralization of the residual sulfuric acid, because of the good distribution of the neutralization agent, this latter reaction could be carried out without any danger of decomposition of hydrogen peroxide through local accumulation of alkali. Furthermore, the suspension finally obtained was flowable and could be centrifuged without further processing.

Example 1

There were dosed into an oxidation mixture consisting of 225 grams of hydrogen peroxide (50 wt. %), and 510 grams of sulfuric acid (96 wt. %), 64 grams of sodium sulfate solution (13 wt. %) and 0.4 grams of tri-n-octylphosphane oxide 287.5 grams of dodecanedioic acid and the mixture heated for 8 hours with stirring at 60° C. After cooling to 20° C. the mixture is treated at this temperature with 1 liter of distilled water and filtered with suction. The residue was washed with cold distilled water and dried.

| The yield of percarboxylic acids was 295 grams ≃ 90.1% of theory | |
|---|---|
| Total AO content was found to be: | 11.56% |
| The dodecanedioic acid balance was: | 96.7% |
| The content of DPDA was: | 94.3% |

Example 2

There was dosed into an oxidation mixture consisting of 170 grams of hydrogen peroxide (50 wt. %) and 204 grams of sulfuric acid (96 wt. %) as well as 1.3 grams of tri-n-octylphosphane oxide, 115 grams of dodecanedioic acid and the mixture heated for 8 hours with stirring at 50° C. After cooling to 8° C. the mixture was treated at this temperature with 300 grams of sodium sulfate solution (13 wt. %) and subsequently neutralized with 507 grams of sodium hydroxide solution (30 wt. %) until a pH of 3.5 was reached and conditioned with 400 grams of sodium sulfate. Subsequently the mixture was centrifuged and dried. Drying was at 40° C.

| The yield of percarboxylic acid was 103.5 grams ≈ 79.0% of theory. | |
|---|---|
| Total AO content was found to be: | 3.86% |
| The dodecanedioic acid balance was: | 88.5% |
| The content of DPDA was: | 34.7% |

| Content and Storage Stability: | | | | |
|---|---|---|---|---|
| | 0 weeks | 4 weeks | 8 weeks | 12 weeks |
| DPDA | 30.9 | 30.5 | 30.5 | 30.1 |
| AO | 3.86 | 3.85 | 3.85 | 3.73 |

Example 3

There were dosed into an oxidation mixture consisting of 102 grams of hydrogen peroxide (50 wt. %) 204 grams of sulfuric acid (96 wt. %) and 25 grams of sodium sulfate solution (13 wt. %) as well as 0.16 grams of tri-n-octylphosphane oxide, 115 grams of dodecanedioic acid and the mixture heated for 8 hours with stirring at 60° C. After cooling to 40° C. the mixture treated at this temperature with 526 grams of sodium sulfate solution (30 wt. %) and subsequently neutralized with 523 grams of sodium hydroxide solution (30 wt. %) until a pH of 3.5 was reached. Subsequently the mixture was centrifuged and dried. Drying was at 40° C.

| The yield of percarboxylic acid was 110.4 grams ≈ 84.3% of theory | |
|---|---|
| The AO content was found to be: | 4.25% |
| The dodecanedioic balance was: | 91.8% |
| The content of DPDA was | 34.3% |

Example 4

There were dosed into an oxidation mixture consisting of 102 grams of hydrogen peroxide (50 wt. %), 204 grams of sulfuric acid (96 wt. %) and 25 grams of sodium sulfate solution (13 wt. %), as well as 0.16 grams of tri-n-octylphosphane oxide, 115 grams of dodecanedioic acid and the mixture heated for 8 hours with stirring at 60° C. After cooling to 40° C. the mixture was treated at this temperature with 394 grams of sodium sulfate solution (30 wt. %) and subsequently neutralized with 523 grams of sodium hydroxide solution (30 wt. %) until a pH of 3.5 was reached and the mixture conditioned with 160 grams of sodium sulfate. Subsequently the product was centrifuged and dried.

| The yield of percarboxylic acid was 112.8 grams ≈ 86.1% of theory | |
|---|---|
| The total AO content was found to be: | 4.27% |
| The dodecanedioic acid balance was: | 95.5% |
| The content of DPDA was: | 34.4% |

Example 5

There were dosed into an oxidation mixture consisting of 127 grams of hydrogen peroxide (50 wt. %), 204 grams of sulfuric acid (96 wt. %) and 0.16 grams of tri-n-octylphosphane oxide, 115 grams of dodecanedioic acid and the mixture heated for 8 hours with stirring at 60° C. After cooling to 40° C. the mixture was treated at this temperature with 394 grams of sodium sulfate solution (30 wt. %) and subsequently neutralized with 521 grams of sodium hydroxide solution (30 wt. %) until a pH of 3.5 was reached and the mixture conditioned with 160 grams of solid sodium sulfate. Subsequently the mixture was centrifuged and then dried at 40° C.

| The yield of percarboxylic acid was: 110.4 grams ≈ 84.3% of theory | |
|---|---|
| The total AO content was found to be: | 4.27% |
| The dodecanedioic acid balance was: | 91.8% |
| The content of DPDA was: | 34.4% |

Example 6

There were dosed into an oxidation mixture consisting of 102 grams of hydrogen peroxide (50 wt. %), 204 grams of sulfuric acid (96 wt. %) and 25 grams of sodium sulfate solution (13 wt. %) as well as 1.6 grams of tri-n-octylphosphane oxide, 115 grams of dodecanedioic acid and the mixture heated for 8 hours with stirring at 60° C. After cooling to 40° C. the mixture was treated at this temperature with 263 grams of sodium sulfate solution (30 wt. %) and subsequently neutralized with 526 grams of sodium hydroxide solution (30 wt. %) until a pH of 3.5 was reached and the mixture conditioned with 160 grams of sodium sulfate. Subsequently the mixture was centrifuged and dried.

| The yield of percarboxylic acid was: 118.3 grams ≈ 90.3% of theory. | |
|---|---|
| The total AO content was found to be: | 4.25% |
| The dodecanedioic acid balance was: | 97.5% |
| The content of DPDA was: | 34.4% |

Example 7

There were dosed into an oxidation mixture consisting of 102 grams of hydrogen peroxide (50 wt. %), 204 grams of sulfuric acid (96 wt. %) and 25 grams of sodium sulfate solution (13 wt. %) as well as 0.16 grams of tri-n-octylphosphane oxide, 115 grams of dodecanedioic acid and the mixture heated for 6 hours with stirring at 60° C. After cooling to 40° C. the mixture was treated at this temperature with 526 grams of sodium sulfate solution (30 wt. %) and subsequently neutralized with 521 grams of sodium hydroxide solution (30 wt. %) until a pH of 3.5 was reached and the mixture conditioned with 120 grams of sodium sulfate. Subsequently the solids were separated from the liquid and dried.

| The yield of percarboxylic acid was 122.8 grams ≈ 93.7% of theory. | |
|---|---|
| The total AO content was found to be: | 4.76% |
| The dodecanedioic acid balance was: | 97.7% |
| The content of DPDA was: | 40.0% |

Example 8

There were dosed into an oxidation mixture consisting of 102 grams of hydrogen peroxide (50 wt. %), 204 grams of sulfuric acid (96 wt. %) and 25 grams of sodium sulfate solution (13 wt. %), as well as 0.16 grams of tri-n-octylphosphane oxide, 115 grams of dodecanedioic acid and the mixture heated for 6 hours with stirring at 60° C. After cooling to 40° C. the mixture was treated at this temperature with 526 grams of sodium sulfate solution (30 wt. %) and subsequently neutralized with 521 grams of sodium hydroxide solution (30 wt. %) until a pH of 3.5 was reached and the mixture conditioned with 80 grams of sodium sulfate. Subsequently the solids were separated and dried.

| The yield of percarboxylic acid was: 118.1 grams ≈ 90.1% of theory. | |
| --- | --- |
| The total AO content was found to be: | 5.30% |
| The dodecanedioic acid balance was: | 96.5% |
| The content of DPDA was: | 43.4% |

Example 9

There were dosed into an oxidation mixture consisting of 102 grams of hydrogen peroxide (50 wt. %), 204 grams of sulfuric acid (96 wt. %) and 25 grams of sodium sulfate solution (13 wt. %), as well as 0.16 gram of tri-n-octylphosphane oxide, 115 grams of dodecanedioic acid and the mixture heated for 6 hours with stiring at 60° C. After cooling to 40° C. the mixture was treated at this temperature with 526 grams of sodium sulfate solution (30 wt. %) and subsequently neutralized with 521 grams of sodium hydroxide solution (30 wt. %) until a pH of 3.5 was reached and the mxxture conditioned with 40 grams of sodium sulfate. Subsequently the solids were separated from the liquid and dried.

| The yield of percarboxylic acid was: 116.7 grams ≈ 89.1% of theory. | |
| --- | --- |
| The total AO content was found to be: | 7.02% |
| The dodecanedioic acid balance was: | 94.5% |
| The content of DPDA was: | 57.5 |

What is claimed is:

1. In a process for the production of a water insoluble peroxycarboxylic acid containing 6 to 16 carbon atoms by reaction of the corresponding aliphatic carboxylic acid having 6 to 16 carbon atoms or aromatic carboxylic acid having 7 to 9 carbon atoms with hydrogen peroxide in the presence of water and sulfuric acid, the improvement comprising carrying out the reaction in the presence of a phosphane oxide of the formula

where $R_1$, $R_2$, and $R_3$ are alkyl, cycloalky, aralkyl, or aryl, the phosphane oxide being used in an amount of 0.01 to 10 wt. % based on the active oxygen employed.

2. A process according to claim 1 wherein the carboxylic acid is an alkanoic acid having 6 to 16 carbon atoms, an alkanedioic acid having 6 to 16 carbon atoms or an aromatic hydrocarbon carboxylic acid having 7 to 9 carbon atoms.

3. A process according to claim 2 wherein the carboxylic acid is an alkanedioic acid having 9 to 13 carbon atoms.

4. A process according to claim 3 wherein the carboxylic acid is dodecanedioic acid.

5. A process according to claim 2 wherein the phosphane oxide is a trialkylphosphane oxide in which each alkyl group has 4 to 18 carbon atoms.

6. A process according to claim 5 wherein each alkyl group in the phosphane oxide has 6 to 10 carbon atoms.

7. A process according to claim 6 wherein the phosphane oxide is tri-n-octylphosphane oxide.

8. A process according to claim 7 wherein the phosphane oxide is used in an amount of 0.01 to 7 wt. % based on the active oxygen employed.

9. A process according to claim 2 wherein the phosphane oxide is used in an amount of 0.01 to 7 wt. % based on the active oxygen employed.

10. A process according to claim 2 wherein the molar ratio of hydrogen peroxide to carboxylic acid is from 1 to 10:1.

11. A process according to claim 10 wherein the molar ratio of hydrogen peroxide to carboxylic acid is from 1.5 to 3:1.

12. A process according to claim 11 wherein the molar ratio of sulfuric acid to carboxylic acid is from 2 to 4:1.

13. A process accordng to claim 10 wherein the molar ratio of sulfuric acid to carboxylic acid is from 1 to 10:1.

14. A process according to claim 2 wherein the molar ratio of sulfuric acid to carboxylic acid is from 1 to 10:1.

15. A process according to claim 1 comprising adding a phlegmatizing agent.

16. A process according to claim 2 comprising adding a phlegmatizing agent.

17. A process according to claim 16 wherein the phlegmatizing agent comprises an aqueous alkali, magnesium, alkaline earth or earth metal sulfate.

18. A process according to claim 17 wherein the phlegmatizing agent comprises a sodium sulfate solution.

19. A process according to claim 8 comprising adding an aqueous sodium sulfate solution as a phlegmatizing agent.

20. A process according to claim 18 comprising also adding aqueous sodium aluminate solution as an additional phlegmatizing agent.

21. A process according to claim 17 comprising adding an aqueous aluminate solution as an additional phlegmatizing agent.

22. A process according to claim 16 comprising adding an aqueous alkali aluminate solution as a phlegmatizing agent.

23. A process according to claim 16 comprising adding an aqueous solution of sodium meta borate.

24. A process according to claim 16 wherein the reaction between the carboxylic acid, hydrogen peroxide, sulfuric acid, water and phosphane oxide is carried out at a temperature of 40° to 70° C. and the process includes the step of cooling the reaction mixture to a lower temperature of 40° to 5° C. and then adding the phlegmatizing agent.

25. A process according to claim 24 wherein the phlegmatizing agent comprises aqueous alkali, magnesium, alkaline earth or earth metal sulfate.

26. A process according to claim 16 wherein the reaction between the carboxylic acid, hydrogen peroxide, sulfuric acid, water and phosphane oxide is carried out at a temperature of 45° to 60° C. and the process includes the step of cooling the reaction mixture to lower temperature of 45°–5° C., adding an alkali sulfate solution and then adding aqueous alkali hydroxide or alkali carbonate in an amount sufficient to adjust the pH to 2 to 6.

27. A process according to claim 26 wherein the cooling is done to 40°–32° C.

28. A process according to claim 2 wherein the carboxylic acid is azelaic acid, dodecanedioic acid or brassylic acid.

29. A dry composition comprising (a) a water insoluble peroxycarboxylic acid having 6 to 16 carbon atoms which is an alkanoic acid, an alkanedioic acid, or an aromatic hydrocarbon carboxylic acid, (2) 0.01 to 10 wt. % of a phosphane oxide of the formula

where $R_1$, $R_2$, and $R_3$ are alkyl having 6 to 16 carbon atoms in each alkyl group, cycloalkyl, aryl, or aralkyl based on the active oxygen present, and (3) a phlegmatizater.

30. A product according to claim 29 including 0.1 to 7 wt. % of the phosphane oxide based on the active oxygen present.

31. A product according to claim 30 wherein the phosphane oxide is a trialkylphosphane oxide having 6 to 10 carbon atoms in each alkyl group.

32. A product according to claim 31 wherein the phosphane oxide is trioctylphosphane oxide.

33. A product according to claim 30 including sodium sulfate as a dephlegmatizer.

34. A product according to claim 33 wherein the sodium sulfate is present in an amount up to 80 wt. %.

35. Peroxydodecanedioic acid containing 0.1 to 1.22 wt. % of trioctylphosphane oxide and 0 to 80 wt. % of sodium sulfate.

36. A process according to claim 1 wherein $R_1$, $R_2$, and $R_3$ are alkyl of up to 18 carbon atoms, cycloalkyl of 5 to 6 carbon atoms, phenyl, benzyl, or tolyl.

37. A composition according to claim 29 wherein $R_1$, $R_2$, and $R_3$ are alkyl of 6 to 10 carbon atoms, cycloalkyl of 5 to 6 carbon atoms, phenyl, benzyl or tolyl.

38. A process according to claim 1 wherein the molar ratio of sulfuric acid to carboxylic acid is from 1 to 10:1.

* * * * *